(12) United States Patent
Beck et al.

(10) Patent No.: US 8,629,411 B2
(45) Date of Patent: Jan. 14, 2014

(54) PHOTOLUMINESCENCE SPECTROSCOPY

(75) Inventors: Markus E. Beck, Scotts Valley, CA (US); Janice C. Lee, Sunnyvale, CA (US); Erel Milshtein, Cupertino, CA (US)

(73) Assignee: First Solar, Inc., Perrysburg, OH (US)

( * ) Notice: Subject to any disclaimer, the term of this patent is extended or adjusted under 35 U.S.C. 154(b) by 229 days.

(21) Appl. No.: 13/181,724

(22) Filed: Jul. 13, 2011

(65) Prior Publication Data

US 2012/0012756 A1    Jan. 19, 2012

Related U.S. Application Data

(60) Provisional application No. 61/363,894, filed on Jul. 13, 2010.

(51) Int. Cl.
*G01J 1/58* (2006.01)
*G01R 31/265* (2006.01)

(52) U.S. Cl.
USPC .................................. 250/458.1; 356/237.2

(58) Field of Classification Search
USPC ................. 250/338.3, 339.04, 458.1, 459.1; 356/237.2, 237.5; 438/14, 16
See application file for complete search history.

(56) References Cited

U.S. PATENT DOCUMENTS

| | | |
|---|---|---|
| 4,671,651 A | 6/1987 | Toyoda et al. |
| 5,118,200 A | 6/1992 | Kirillov et al. |
| 5,213,985 A | 5/1993 | Sandroff et al. |
| 5,388,909 A | 2/1995 | Johnson et al. |
| 5,399,504 A | 3/1995 | Ohsawa |
| 6,116,779 A | 9/2000 | Johnson et al. |
| 6,122,042 A | 9/2000 | Wunderman et al. |
| 6,534,774 B2 | 3/2003 | Hasegawa et al. |
| 6,911,347 B2 | 6/2005 | Higgs |
| 7,098,052 B2 | 8/2006 | Higgs |
| 7,113,276 B1 | 9/2006 | Higgs et al. |
| 7,446,321 B2 | 11/2008 | Laurent et al. |
| 7,504,642 B2 | 3/2009 | Hummel et al. |
| 7,589,834 B2 | 9/2009 | Higgs |
| 2007/0008526 A1 | 1/2007 | Buczkowski |
| 2007/0176119 A1 | 8/2007 | Hummel |
| 2009/0051914 A1 | 2/2009 | Trupke et al. |
| 2011/0117681 A1 | 5/2011 | Bardos et al. |
| 2011/0211763 A1* | 9/2011 | Maier et al. .................... 382/218 |

FOREIGN PATENT DOCUMENTS

| | | |
|---|---|---|
| JP | 2003-227758 A | 8/2003 |
| JP | 2008-230895 A | 10/2008 |
| WO | WO 2004/010121 A1 | 1/2004 |
| WO | WO 2010/019992 A1 | 2/2010 |
| WO | WO 2010/022962 A1 | 3/2010 |
| WO | WO 2010/142270 A1 | 12/2010 |
| WO | WO-2011/017775 A1 | 2/2011 |

* cited by examiner

*Primary Examiner* — Mark R Gaworecki

(74) *Attorney, Agent, or Firm* — Dickstein Shapiro LLP

(57) ABSTRACT

This invention relates to temperature-corrected photoluminescence spectroscopy which may be applied to semiconductors and, in particular, photovoltaic films.

38 Claims, 7 Drawing Sheets ured device for measuring material temperature.
PHOTOLUMINESCENCE SPECTROSCOPY This application claims priority under 35 U.S.C. §119(e) to Provisional Application No. 61/363,894, filed on Jul. 13, 2010, which is incorporated herein by reference.

TECHNICAL FIELD

This invention relates to temperature-corrected photoluminescence spectroscopy which may be applied to semiconductors and, in particular, photovoltaic films.

BACKGROUND

Photoluminescence spectroscopy may be used to characterize material properties of a semiconductor in a thin film photovoltaic module. In particular, photoluminescence spectroscopy may be used to characterize bandgap, defect densities, and recombination mechanisms in the semiconductor. Unfortunately, existing photoluminescence techniques are only useful when the semiconductor is at a temperature between room temperature and absolute zero.

DETAILED DESCRIPTION

Figure 1:
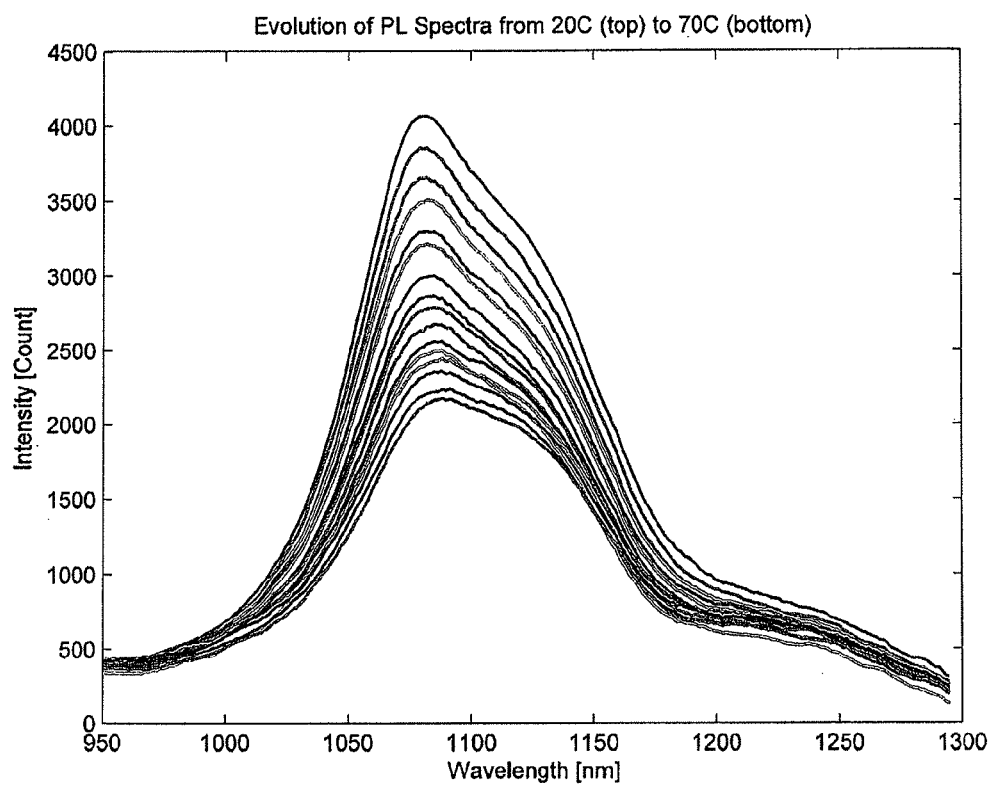
FIG. 1 is a graph of power versus wavelength for a sample at temperatures ranging from 20° C. to 70° C.

Photovoltaic devices can include multiple layers formed on a substrate (or superstrate). Copper indium gallium selenide (CIGS) based photovoltaic devices can be made from high temperature vacuum processes, such as co-evaporation, reaction of stacked elemental layers, or selenization of metal precursors. For example, a photovoltaic device can include a transparent conductive oxide (TCO) layer, a buffer layer, a semiconductor layer, and a conductive layer formed adjacent to a substrate. The semiconductor layer can include a semiconductor window layer and a semiconductor absorber layer, which can absorb photons. The semiconductor absorber layer can include CIGS. Each layer in a photovoltaic device can be created (e.g., formed or deposited) by any suitable process and can cover all or a portion of the device and/or all or a portion of the layer or substrate underlying the layer. For example, a "layer" can mean any amount of any material that contacts all or a portion of a surface.

It can be desirable to utilize various analytical techniques to measure various characteristics of a semiconductor layer in a photovoltaic module. Photoluminescence is a non-destructive technique used to characterize material properties of a semiconductor. Material properties such as electronic bandgap, defect densities, and recombination mechanisms can be determined through PL analysis. By determining the bandgap, PL provides a way to quantify the elemental composition of a semiconductor. Quantifying the elemental composition of the semiconductor allows impurities to be identified. The PL often reveals spectral peaks associated with impurities in the host material. The high sensitivity of the PL technique allows for identification of intentional and unintentional impurities that can significantly affect material quality and device performance. In addition to impurity concentrations, defect concentrations are also revealed.

Photoluminescence relies on the creation of electron-hole pairs by incident radiation and the detection of the subsequent photon emission from radiative recombination. The quantity of PL emitted from a material is directly related to the relative amount of radiative and nonradiative recombination rates. Since nonradiative rates are typically associated with impurities, the PL technique can quantify a reduction in material quality between two points in the manufacturing process. In a typical PL setup, a sample is illuminated by a laser having frequency $\nu$ such that the energy of the excitation photons $h\nu$ is larger than the energy gap (Eg) corresponding to the excitation. The light emitted from the material is focused on a spectrometer to obtain emission intensity as a function of wavelength.

The emitted photon energy depends on the recombination process such as band-to-band or excitonic recombination, while the emission intensity is proportional to the density of recombination centers. The sample volume probed in photoluminescence is determined by the penetration depth of the exciting laser wavelength in the substrate material. Samples are sometimes cooled to cryogenic temperatures, especially in a research setting, to minimize thermally activated nonradiative recombination process and thermal line broadening of the photoluminescence emission peak.

Photoluminescence can be used as a characterization technique in photovoltaic films such as, for example, CIGS to understand material quality and defect formation. The bandgap of the material can be obtained from the dominant emission energies. In CIGS, the measurement of band gap indirectly provides information for the gallium to indium content ratio, as well as the indication of the transition from the copper-rich to copper-poor phase during film growth. Photoluminescence can be used to observe, for example, emission energies for $CuIn_xGa_{1-x}Se_2$ with different gallium to indium content ratios and the onset of transition from copper-rich phase to copper-poor phase indicated by a change in energy gap. The information depth can be adjusted via the incident laser frequency, as long as the incident light has sufficient energy $h\nu > Eg$. Of particular importance is information from the depth representing the width of the space charge region. Integrated PL intensity is an indicator of material quality. An increase in intensity corresponds to fewer defect energy states and hence an increase in minority-carrier lifetime. Photoluminescence yield from a sample including a molybdenum substrate can be reduced due to increased rear-surface recombination velocity from the Mo substrate. A room-temperature PL yield of $CuIn_{1-x}Ga_xSe_2$ on glass substrate can be compared to the same material on a Mo substrate for different gallium contents. Such observation can be made at any suitable temperature, for example approximately room temperature, which can be about 25 degrees C. In this example, lower yield is detected for molybdenum due to rear-surface recombination loss. A combination of PL and absorption measurements can be used to extract the upper limit of achievable open-circuit voltage, which is useful to predict electrical performance of the final photovoltaic device.

Known photoluminescence (PL) techniques are only useful when the semiconductor is at or below room temperature.

Expanding the range of PL techniques to higher temperatures is desirable, because it enables PL to be incorporated into manufacturing processes where semiconductors are often at elevated temperatures. This capability has been invented and is described herein.

Tables of low-temperature PL data are known and have been compiled for semiconductors below room temperature. In fact, much of the low-temperature PL data was collected near absolute zero to reduce thermal noise within the data. To make use of this data, it is necessary to cool the semiconductor to a temperature below room temperature before measuring PL during the manufacturing process. This cooling step wastes time and energy.

To overcome this problem, an apparatus and method have been invented which allows PL to be measured while the semiconductor is at an elevated temperature on the assembly line. This produces high-temperature PL data. By correcting the high-temperature PL data for temperature, oxygen concentration, and water vapor, the data can be converted to temperature-corrected data and compared directly against existing tables of low-temperature PL data to identify material properties of the semiconductor. As a result, a PL measuring apparatus can be integrated into the assembly line, and PL can be measured in-process, thereby allowing for enhanced productivity and improved quality control. This apparatus and method work particularly well with copper indium gallium selenium (CIGS) photovoltaic (PV) films.

High-temperature photoluminescence data for semiconductor materials are not available in the scientific literature, since PL data are commonly measured at low temperature, e.g., absolute zero to approximately room temperature, or about 25 degrees C., to reduce thermal noise. These data are referred to herein as "low-temperature PL data." Since reliable high-temperature data are unavailable, it is necessary to develop an apparatus and method for applying temperature correction to the high-temperature PL data. In doing so, PL data can be collected and evaluated in-process, and the cooling step can be eliminated. Elimination of the cooling step is particularly useful when manufacturing CIGS-based PV modules, since the semiconductor material is typically near 150° C. at the end of the deposition process. The method described herein allows for measurement of the PL signature during the CIGS process without the need to cool the substrate to near or below room temperature.

The ambient gas composition through which the laser beam and emitted light must travel affects the PL data. For example, when the ambient composition has a high oxygen content, the oxygen facilitates surface oxidation of the CIGS absorber and results in irreversible degradation in integrated photoluminescence intensity. Water vapor also attenuates the integrated photoluminescence intensity. As a result, it may be necessary to correct the measured PL data for variations in the ambient gas composition, since manufacturing does not typically occur in an inert environment.

To overcome the aforementioned issues, temperature correction may be employed as well as using a controlled ambient gas composition. A method may include determining the sensitivity of a photoluminescence peak intensity, a total integrated intensity under the spectrum, full width at half maximum (FWHM), and a peak wavelength shift with sample temperature. These items may be determined for a compositional range of interest (e.g. CGI, GGI, Se/M) and a particular photoluminescence setup. The method may also include measuring the temperature of the sampled location of the photoluminescence analysis or interpolating the temperature at the sampled location from multiple neighboring locations proximate to the sampled location. In addition, the method may include determining the shift in photoluminescence intensity and the shift in wavelength that are needed to correct for the temperature of the analysis spot. The required shift in photoluminescence intensity and wavelength may be determined from a calibration table. The wavelength and peak intensity determination may require additional information about the approximate composition of the specimen to reduce the error of the temperature correction. This additional information may be provided through x-ray fluorescence of a representative semiconductor.

In one aspect, an in-line apparatus for measuring photoluminescence from a material on a substrate in a manufacturing process can include a light source configured to direct light along a light path through a lens onto a material deposited on a substrate positioned in a process chamber. The apparatus can include a spectrometer configured to receive light emitted from the material and generate photoluminescence data for the material. The apparatus can include a temperature measurement device configured to measure the temperature of the material.

The light source can include a laser. The laser can have a power ranging from about 0 mW to about 400 mW. The laser can have a power ranging from about 30 mW to about 100 mW. The light focused onto the material can have a spot size of less than about 3 $mm^2$. The light focused onto the material can have a spot size of about 1 $mm^2$. The temperature measurement device can include an infrared pyrometer. The apparatus can include a first optical fiber to direct light from the light source. The apparatus can include a second optical fiber to transmit the light emitted from the material.

The apparatus can include a computer configured to receive a high-temperature photoluminescence data set from the spectrometer and a measured temperature from the temperature measurement device. The computer can include a low-temperature photoluminescence data set and a temperature correction equation describing the relation of photoluminescence to temperature for the material. The computer can read the measured temperature and can apply the temperature correction equation to the high-temperature photoluminescence data set to produce a temperature-corrected photoluminescence data set. The computer can compare the temperature-corrected photoluminescence data set to the low-temperature photoluminescence data set.

The computer can identify material properties of the material based upon the temperature-corrected photoluminescence data set. The material properties include bandgap. The material properties include defect density. The material properties include recombination mechanisms. The apparatus can include at least one additional lens through which the light passes and is converted between a focused light beam and a collimated light beam.

In another aspect, a system for measuring photoluminescence from a material on a substrate in a manufacturing process can include a substrate process chamber and a light source configured to direct light along a light path through a first lens toward a substrate position in the process chamber. The system can include a spectrometer configured to receive light emitted from the material and generate photoluminescence data for the material. The system can include a temperature measurement device configured to measure the temperature of the material. The system can include at least one additional measurement device configured to measure a characteristic of the process chamber environment.

The system can include a substrate positioned at the substrate position in the process chamber. The substrate can include a material deposited on the surface of the substrate. The material can include a semiconductor material. The semiconductor material can include copper indium gallium (di) selenide. The semiconductor material can include cadmium telluride. The system can include a second lens positioned proximate to the first lens to form an apparatus head configured to apparatus head configured to convert focused light to collimated light and collimated light to focused light. The apparatus head can be positioned in the process chamber. The apparatus head can be positioned outside the process chamber and the process chamber can include a window to allow light from the light source to be directed into the process chamber.

The system can include a first optical fiber to direct light from the light source to the apparatus head. The system can include a second optical fiber to transmit light from the apparatus head to the spectrometer. The system can include a water vapor measurement device configured to measure the water vapor concentration inside the process chamber. The system can include an oxygen measurement device configured to measure the oxygen concentration inside the process chamber.

The system can include a computer configured to correct photoluminescence data obtained from the material, wherein the correction is based on one or more of material temperature, oxygen concentration inside the process chamber, or water concentration inside the process chamber. The system can include a conveyor configured to position the substrate at the substrate position in the process chamber. The substrate has a temperature of between about 25 degrees C. and about 400 degrees C. The substrate has a temperature of between about 25 degrees C. and about 300 degrees C. The substrate has a temperature of between about 25 degrees C. and about 200 degrees C.

In another aspect, a test apparatus for measuring photoluminescence from a semiconductor can include a test chamber comprising a window, wherein the chamber is configured to receive a material to be tested. The apparatus can include a first optical fiber configured to transmit light from a laser to a lens, wherein the lens is configured to focus the light from the first optical fiber through the window and onto the semiconductor. The apparatus can include a second optical fiber configured to collect and transmit light emitted from the semiconductor to a spectrometer. The apparatus can include a temperature measurement device disposed within the chamber.

The lens can be connected to a micro-adjustment device which permits the lens to move linearly toward or away from the semiconductor. The test chamber can include a first clip to secure the semiconductor against an inner surface of the test chamber. The test chamber can include a second clip to secure the temperature measurement device against the semiconductor. The apparatus can include an oxygen concentration sensor disposed within the test chamber. The temperature measurement device can be a thermocouple. The apparatus can include a heater disposed within the test chamber. The apparatus can include a water vapor sensor disposed within the test chamber. The test chamber can include an inlet configured to transport gas into the test chamber and an outlet configured to transport gas out of the test chamber. The apparatus can include a vacuum pump connected to the outlet. The apparatus can include a nitrogen source connected to the inlet. The apparatus can include a heat source capable of maintaining the semiconductor in a module manufacture temperature range. The module manufacture temperature range is between 25 degrees C. and 300 degrees C.

In another aspect, a method for determining material properties of a semiconductor at a temperature greater than room temperature can include providing light from a laser onto a surface of a semiconductor. The method can include collecting a high-temperature photoluminescence data set from the semiconductor. The method can include measuring the semiconductor temperature. The method can include providing a temperature correction equation describing the relation of photoluminescence to temperature for the semiconductor. The method can include applying the temperature correction equation to the high-temperature photoluminescence data set to produce a temperature-corrected photoluminescence data set.

The method can include measuring oxygen concentration proximate to the semiconductor. The method can include providing an oxygen concentration correction equation describing the relation of photoluminescence to oxygen concentration for the semiconductor. The method can include applying the oxygen concentration correction equation to the temperature-corrected photoluminescence data set. The method can include measuring water vapor concentration proximate to the semiconductor. The method can include providing a water vapor concentration correction equation describing the relation of photoluminescence to water vapor concentration for the semiconductor. The method can include applying the water vapor concentration correction equation to the temperature-corrected photoluminescence data set. The method can include providing a low-temperature photoluminescence data set. The method can include comparing the temperature-corrected photoluminescence data set against the low-temperature photoluminescence data set to determine material properties of the semiconductor.

In another aspect, a multilayered structure can include a substrate and a semiconductor material deposited on the substrate, wherein high-temperature photoluminescent data of the semiconductor material have been corrected by providing light from a laser onto a surface of the semiconductor material, collecting the high-temperature photoluminescence data from the semiconductor material, measuring the semiconductor temperature, providing a temperature correction equation describing the relation of photoluminescence to temperature for the semiconductor, and applying the temperature correction equation to the high-temperature photoluminescence data to produce temperature-corrected photoluminescence data. The semiconductor material can include a semiconductor absorber material.

As discussed above, low-temperature photoluminescence data are available in scientific literature whereas high-temperature photoluminescence data are not. Applying a PL technique to semiconductors during the manufacturing process results in high-temperature PL data being collected at any suitable temperature, for example, from about 25 degrees C. to about 400 degrees C., to about 300 degrees C., or to about 200 degrees C. To accurately interpret this data, it must be temperature-corrected to compensate for the temperature effect on the data set. By compensating for the temperature effect on the data set, the data can be compared to low-temperature PL data. This allows the material properties of the semiconductor to be accurately identified. By quantifying the shape, intensity, full width at half maximum (FWHM), and center wavelength of the PL spectra, material properties of the semiconductor can be identified.

Figure 2:
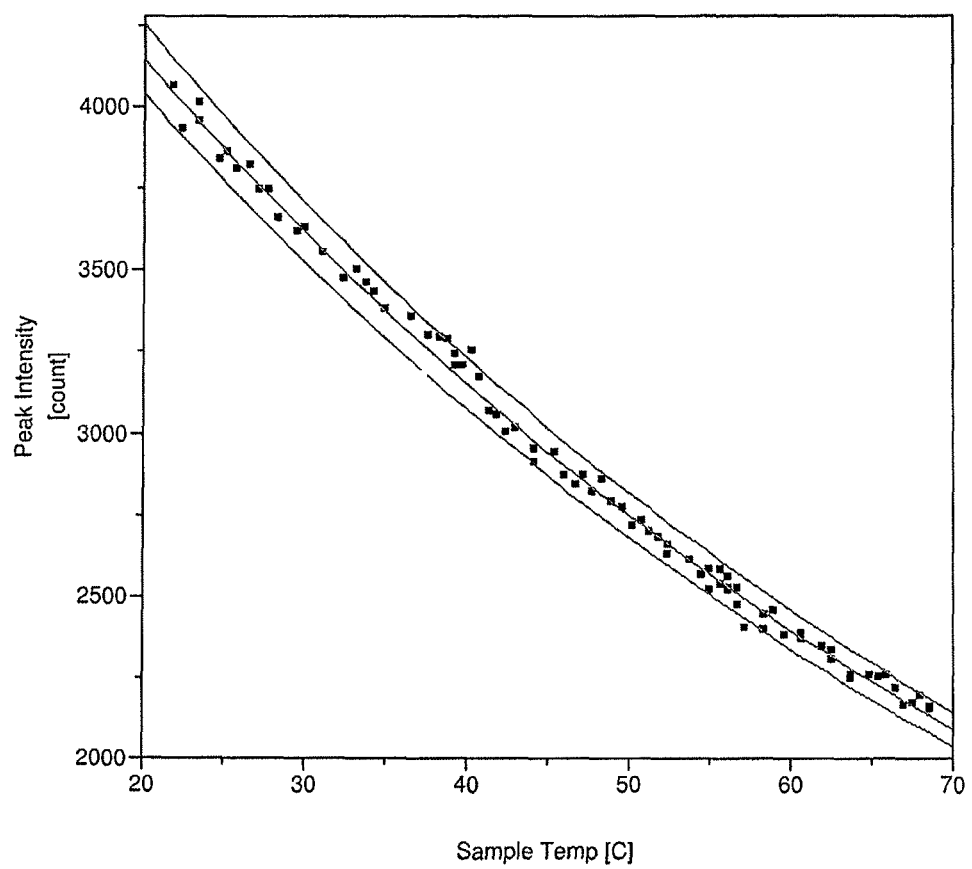
FIG. 2 is a graph of maximum peak count versus temperature, with a line of best fit to functional form exp(T) based on data presented in FIG. 1.

To apply temperature-correction to the high-temperature PL data, the semiconductor's PL response to temperature variation can be quantified. This can be accomplished by running an experiment where the temperature of the semiconductor is swept across a range of temperatures and the PL signal is measured during the temperature sweep. High-temperature photoluminescence data for a CIGS absorber was measured from room temperature to an elevated temperature. FIG. 1 shows the evolution of a photoluminescence spectrum from 20° C. up to 70° C. in a pure nitrogen environment. The peak intensity decays with increasing temperature with an exp(T) dependence as shown in FIG. 2. Functional relationships other than exp(T) are also possible, depending on the sample material. By integrating the area under each curve, an integrated photoluminescence intensity can be calculated at each temperature. Although this data may only be useful for the specific semiconductor tested, a similar methodology can be applied to any semiconductor of interest.

If a specific type of semiconductor is being manufactured, a sample of that semiconductor can be subjected to a temperature sweep while its PL signal is recorded. To ensure an adequate semiconductor is selected for test purposes, the semiconductor may be subjected to x-ray fluorescence (XRF) where the material is excited through bombardment of high-energy x-rays or gamma rays. This technique provides an elemental analysis of the semiconductor. In a CIGS absorber, the XRF technique may reveal the compositional characteristics of the CIGS layers. For example, the CGI and GGI ratios may be revealed, where CGI=Cu/(Ga+In) and GGI=Ga/(Ga+In).

Oxygen concentration near the semiconductor can affect the PL signal. Oxygen can facilitate surface oxidation of the CIGS absorber and results in degradation of integrated PL intensity. The actual effect of oxygen concentration may be quantified experimentally. The effect of oxygen concentration may be determined by collecting PL signals across a range of oxygen concentrations. This may be accomplished by increasing the quantity of nitrogen in the chamber to displace oxygen. Alternately, the test may begin with pure nitrogen in the chamber, and the oxygen concentration may be increased by adding pure oxygen to the chamber. A maximum acceptable oxygen concentration can be identified for which PL signal integrity is preserved (e.g., not degraded). Subsequent high-temperature PL measurements can be performed in an environment controlled to maintain an acceptable oxygen concentration.

Water vapor can also result in degradation of integrated PL intensity, since water molecules absorb portions of the electromagnetic spectrum. Additionally, the presence of moisture in a process chamber can cause oxidation of a deposited material. Water has a complex absorption spectrum, with strong absorption occurring at wavelengths around 1450, 1950, and 2500 nm and weaker absorption occurring around 970 and 1200 nm. Also, water has three additional sets of absorption lines in the infrared spectrum near 730, 820, and 930 nm. To accurately identify material properties based on the measured PL signal, the absorption effects of water must be accounted for. Before it can be accounted for, it must be quantified. The effect of water vapor on PL may be quantified experimentally or theoretically. To quantify the effect experimentally, the concentration of water vapor in the chamber may be swept from a low value to a high value and PL recorded across the sweep. Alternately, since the effect of water vapor on PL is well documented, it may be approximated based on available data.

The material temperature, the oxygen concentration in the process chamber, and the water vapor concentration in the process chamber, and any combinations thereof, can be accounted for to yield a corrected photoluminescent data set, which can compensate for each of these variables and/or any possible combination of these variables. As such the derived photoluminescent data can be a function of material temperature and/or oxygen concentration and/or water vapor concentration.

If an equation-based correction can not be used to compensate for oxygen concentration, a maximum acceptable oxygen concentration can be determined inside which range correctable PL measurements can be taken. If an ambient, such as a process chamber ambient, has an oxygen concentration above the acceptable oxygen concentration, the ambient can be regulated to bring the oxygen concentration within the acceptable range for which reliably correctable PL measurements can be taken. For example, nitrogen can be added to the ambient to lower the oxygen concentration to the acceptable range. If an equation-based correction can not be used to compensate for water vapor concentration, a maximum acceptable water vapor concentration can be determined inside which range correctable PL measurements can be taken. If an ambient, such as a process chamber ambient, has a water vapor concentration above the acceptable water vapor concentration, the ambient can be regulated to bring the water vapor concentration within the acceptable range for which reliably correctable PL measurements can be taken.

Figure 3:
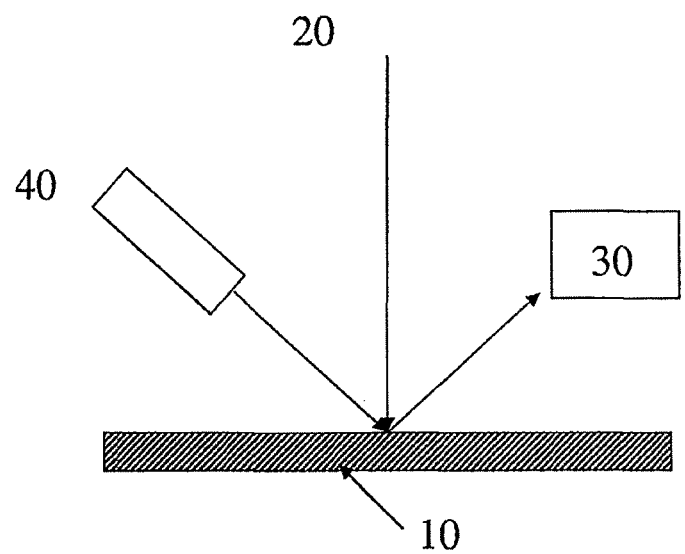
FIG. 3 is an example of a non-contact temperature measurement device for measuring material temperature.

FIG. 3 depicts an embodiment of a test apparatus of the present invention. Sample 10 can include any suitable material, for example, a material such as a semiconductor material deposited on a substrate. Sample 10 can include a material for which one or more of a temperature sweep, oxygen concentration sweep, and/or water vapor sweep have been performed to create a profile for the particular material. Sample 10 can include any other material for which photoluminescent data can be taken, including semiconductors, conductors, or insulators. Sample 10 can include copper, indium, gallium, and/or selenium. Sample 10 can have the formula $CuIn_{1-x}Ga_xSe_2$. Sample 10 can include cadmium telluride. Light source 20 can include any suitable light source, such as a laser. A light beam (e.g., a laser beam) can be directed toward the sample 10. As a result, light can then be reflected off of sample 10 toward a spectrometer 30, which can generate photoluminescence data relating to sample 10.

Sample 10 can be present in a high-temperature environment, for example, an environment having a temperature greater than about 25 degrees C., greater than about 50 degrees C., or greater than about 100 degrees C. The environment can have a temperature of about 25 degrees C. to about 400 degrees C., about 25 degrees C. to about 300 degrees C., or about 25 degrees to about 200 degrees C. The environment can have a temperature of about 25 degrees C. to about 75 degrees C., or about 75 degrees C. to about 100 degrees C., about 100 degrees C. to about 200 degrees C., about 200 degrees C. to about 300 degrees C., or about 300 degrees C. to about 400 degrees C. The environment can be about 125 degrees C. to about 175 degrees C. The apparatus depicted in FIG. 3 can also include a temperature measurement device 40 for taking the temperature of sample 10 and/or proximate to sample 10 before, during, and/or after light from light source 20 is directed at sample 10. Temperature measurement device 40 can include any suitable device, including any suitable pyrometer, thermometer, or thermocouple.

Figure 4:
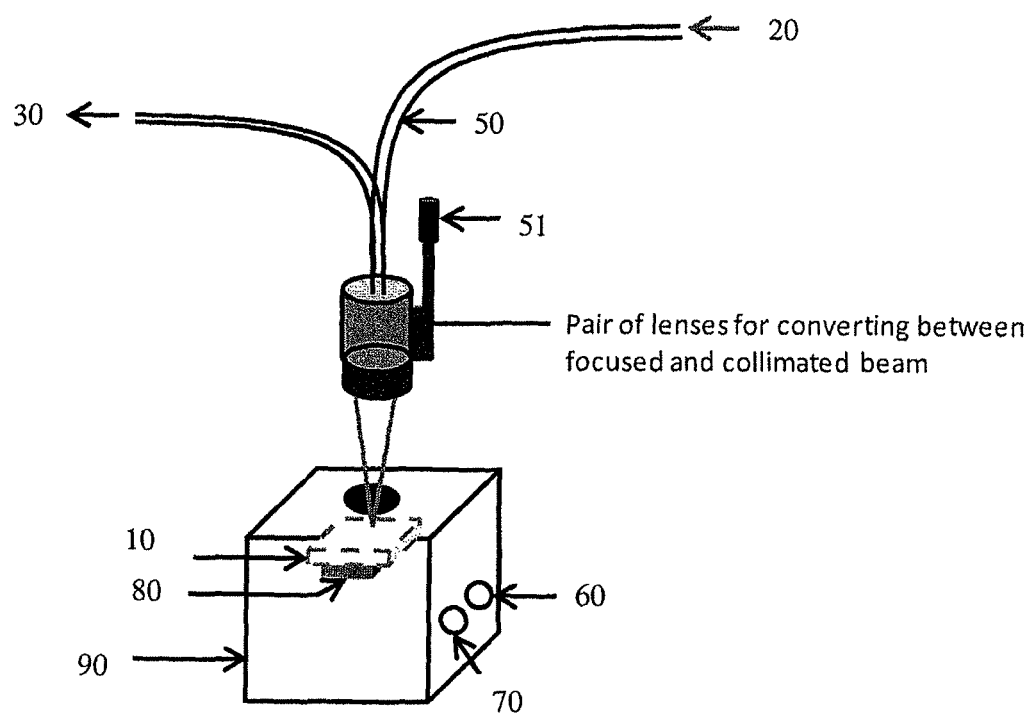
FIG. 4 is an example apparatus for measuring photoluminescence of a material.

FIG. 4 is a detailed depiction of a photoluminescent test apparatus of the present invention. The test apparatus can include a test chamber or can be contained within a chamber. The chamber may be sealable to produce an airtight chamber. The test chamber may include any suitable inlets, outlets, and/or other connections. For example, the apparatus can include a thermocouple inlet port 70 for providing access to the test chamber interior by a thermocouple. For example, the apparatus can include gas inlet 60. Gas inlet 60 can be used to alter or maintain the gas composition of the testing environment. An outlet can be included to permit gas to be pumped into and out of the chamber. By doing so, the gas composition within the test chamber can be controlled. For example, the oxygen concentration in the chamber may be adjusted by pumping nitrogen into the test chamber to displace oxygen. This permits PL testing to be conducted at various oxygen levels, thereby allowing the effect of oxygen concentration on PL signal to be isolated and quantified. The outlet may also allow the test chamber to be purged to create a vacuum, which may be useful for establishing a baseline PL signal. A nitrogen ambient can also be used for establishing a baseline PL signal, for example, in the case of a CIGS material. The test chamber may include a gas composition sensor. For example, the test chamber may include an oxygen composition sensor. The sensor may be configured to measure oxygen concentration near the semiconductor.

The apparatus may include a water vapor sensor configured to measure the concentration of water vapor in the chamber. The water vapor sensor may be a closed-path water vapor sensor based on optical absorption of an atomic argon emission line. Alternately, the water vapor sensor may be a chilled mirror hygrometer, a capacitance-based polymer sensor, or any suitable water vapor sensor.

The test chamber may include a temperature measurement device capable of measuring the temperature of the semiconductor. The temperature measurement device may measure temperature by contacting the semiconductor or by a non-contact method. If a contact method is selected, a thermocouple may be used. Alternately, if a non-contact method is selected, a infrared pyrometer operating, for example, at about 1 to about 100 µm, about 1 to about 50 µm, about 1 to about 20 µm, about 1 to about 5 µm, about 5 to about 7 µm, or about 7 to about 18 µm, may be used to measure the temperature of the semiconductor surface. Other non-contact measurements such as surface electrical impedance may be used. Although three temperature measurement devices are described, these are not limiting. Any suitable temperature measurement device may be used.

The temperature may be taken at the same location on the semiconductor surface where the PL measurement is taken or at a nearby location. The temperature may be taken at one location or at several locations near the PL measurement location. Multiple temperatures may be averaged or interpolated to improve accuracy. To account for changes in temperature over time, the temperature may be taken immediately before and after the PL data has been acquired to determine the average temperature during the analysis. To prevent the laser beam from interfering with the temperature measurement due to scattering into the pyrometer, the laser beam can be blocked during the temperature measurement. Blocking can be achieved with a shutter, filter, or other suitable device. In another embodiment, the photoluminescent measurements can be taken continuously (for example, as a substrate with sample 10 passes through a process chamber), while the temperature and/or oxygen and/or water vapor measurements are performed at a given frequency. Alternatively, the photoluminescent measurements can be taken at a given frequency while one or more of temperature, oxygen concentration, and/or water vapor concentration are taken continuously.

The test apparatus may include heater 80 capable of transferring energy to the semiconductor. Heater 80 may be in direct contact with sample 10. For instance, heater 80 may be disposed within the chamber and sample 10 may rest directly on heater 80, which can be any suitable type of heater, for example, a conductive heater. Alternately, heater 80 may not be in contact with sample 10 and may be positioned anywhere inside or outside of the chamber. For example, heater 80 may be a catalytic heater positioned outside of the chamber and connected to the chamber via ducting that includes a fan to transmit heated air to the chamber. Although two specific examples of heaters are described, these are not limiting. Any suitable heater may be used to maintain and/or adjust the temperature of sample 10. For example heater 80 can be used to maintain and/or adjust the temperature of sample 10 to one or more temperatures commonly used during the manufacture of CIGs-based PV modules. For example, the temperature can be greater than about 25 degrees C., greater than about 50 degrees C., or greater than about 100 degrees C. The temperature can be about 25 degrees C. to about 200 degrees C., about 25 degrees C. to about 300 degrees C., or about 25 degrees to about 200 degrees C. The temperature can be about 25 degrees C. to about 75 degrees C., or about 75 degrees C. to about 100 degrees C., about 100 degrees C. to about 200 degrees C., about 200 degrees C. to about 300 degrees C., or about 300 degrees C. to about 400 degrees C. The temperature can be about 125 degrees C. to about 175 degrees C.

Heater 80 and the temperature measurement device may be connected to a temperature control system. The temperature control system may include a temperature controller and may be capable of receiving a target temperature and ramping the actual temperature, which is read from the temperature measurement device, until it matches the target temperature. The temperature controller may be an OMEGA temperature controller and may be an on-off type, a proportional type, or a proportional with integral and derivative (PID) control type. Alternately, any suitable temperature controller may be used.

The apparatus may include light source 20 such as a laser. The laser can be any suitable type of laser. The light source 20 may be aligned with a first optical fiber 50 having a first end and a second end. The alignment may allow the laser beam to enter the first end of the first optical fiber 50 and exit the second end of the first optical fiber.

The second end of the first optical fiber 50 may be at or proximate to a lens or multiple lenses, or any other suitable optical components. The lens or lenses can be any suitable type of lenses. For example, the lens or lenses can include refractory lenses, reflectance-based lenses, or any combination thereof The lens may be configured to receive the laser beam and focus the laser beam to a spot on sample 10. The spot size may be about 1.0 mm$^2$, although any suitable spot size may be used. The lens may be a single lens or it may be series of lenses or any other suitable combination of optical components. For instance, one or more lens may be used to focus the laser beam onto sample 10. The lens or multiple lenses can also be configured to transform light emitted from sample 10 so the light can be transmitted to spectrometer 30. For example, the lens or multiple lenses can collimate the light so it can be transmitted to spectrometer 30. Light from the lens or lenses can be transmitted by any suitable means. For example, it can be transmitted by a second optical fiber to spectrometer 30. Coupling of light from light source 20 and the light reemitted back to spectrometer 30 can be by a dual-optical fiber. Alternatively, the light can be transmitted through space and/or air to spectrometer 30, for example, using one or more mirrors of suitable type and configuration. The lens or multiple lenses can be configured in an apparatus head.

The lens may be connected to a micro-adjustment device 51 which permits the lens to move linearly toward or away from sample 10. In particular, the lens may be connected to a micro-adjustment device 51 having a thumb knob and a fine thread pitch that allows the lens position to be adjusted by several microns or less per rotation of the thumb knob. By adjusting the position of the lens, the focal point of the lens can be properly directed onto sample 10 to provide a desirable spot size and strong PL signal. In embodiments having multiple lenses, for example, two lenses, a micro-adjustment device 51 can allow a user to move the lenses linearly relative to each other.

A second optical fiber may be positioned proximate to the lens and may be configured to receive light emitted from the semiconductor resulting from laser light being directed onto sample 10. The PL may enter a first end of the second optical fiber and exit a second end of the second optical fiber. The second end of the second optical fiber may be connected to spectrometer 30 used to measure properties of the PL light over a specific portion of the electromagnetic spectrum. By analyzing the PL signal, the material properties of sample 10 may be identified. Sample 10 can be contained in a sample chamber during PL testing.

Figure 5:
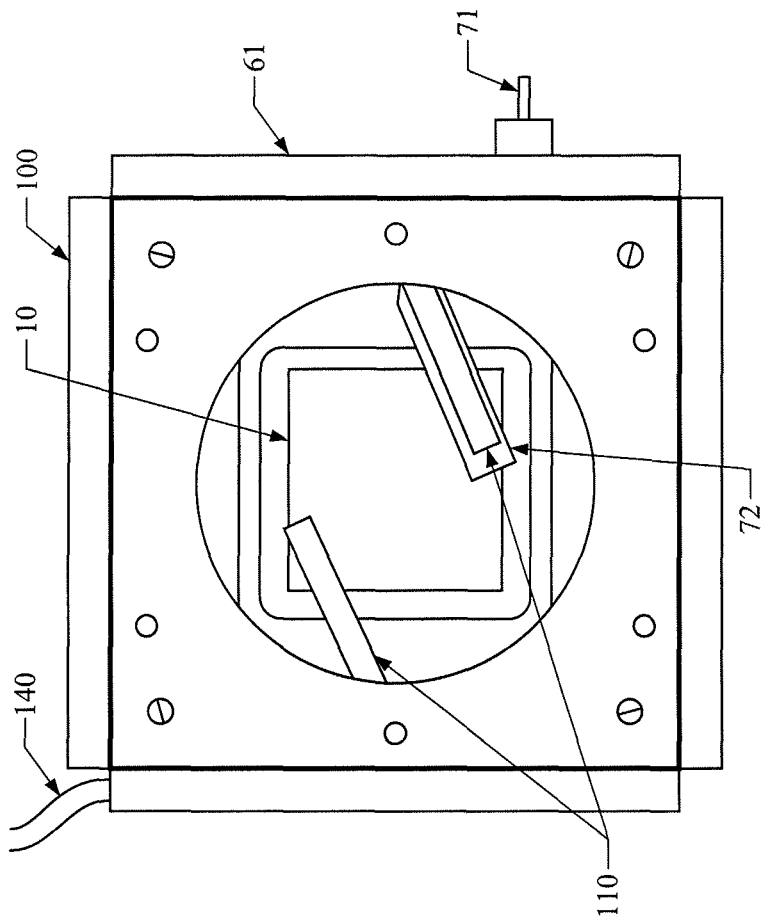
FIG. 5 is an example apparatus for measuring photoluminescence of a material.
Figure 5:
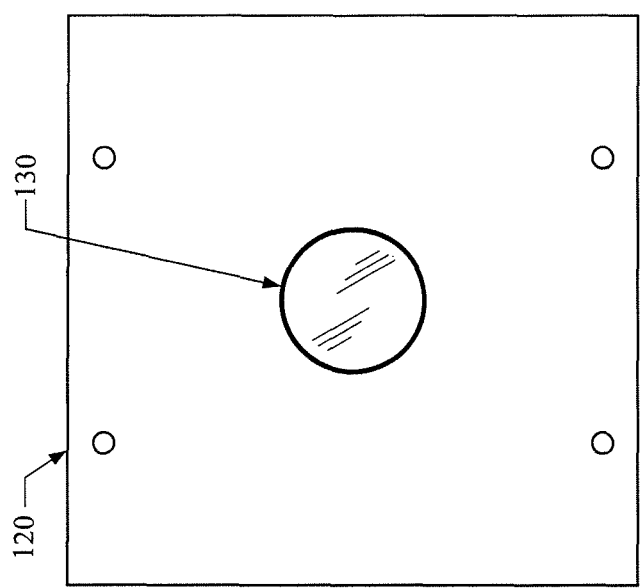

FIG. 5 depicts an alternative embodiment of test chamber 100 configured to containing sample 10 during photoluminescence testing. Test chamber 100 may be any suitable vessel capable of maintaining a constant temperature. For example, test chamber 100 may include a steel container. Alternately, test chamber 100 can include a temperature controlled room or any other suitable chamber configured to receive a semiconductor for testing.

The test chamber 100 may include a removable lid 120. Test chamber lid 120 may include a test chamber window 130 which permits laser light to enter and leave the chamber. Test chamber window 130 may be constructed from Pyrex or any other suitable material having high transmittance. Pyrex is a low-cost and rugged material having 92% transmission for wavelengths between 350 and 2400 nm. Using a window material with a high absorbance is undesirable, because it reduces the PL signal and, therefore, requires greater laser power to acquire a usable PL signal. Test chamber 100 may be sealable to produce an airtight chamber and can include clips 110 to secure sample 10 within Test chamber 100. Test chamber 100 can include any suitable inlets, outlets, and/or other connections. For example, test chamber 100 can include a gas inlet 61, as well as thermocouple 71 and thermocouple tip 72 to measure to temperature of sample 10 during photoluminescence testing. The thermocouple tip 72 may be contacted to sample 10. Test chamber 100 can include an electrical connection 140, such as a power connection for an integral heater.

Figure 6:
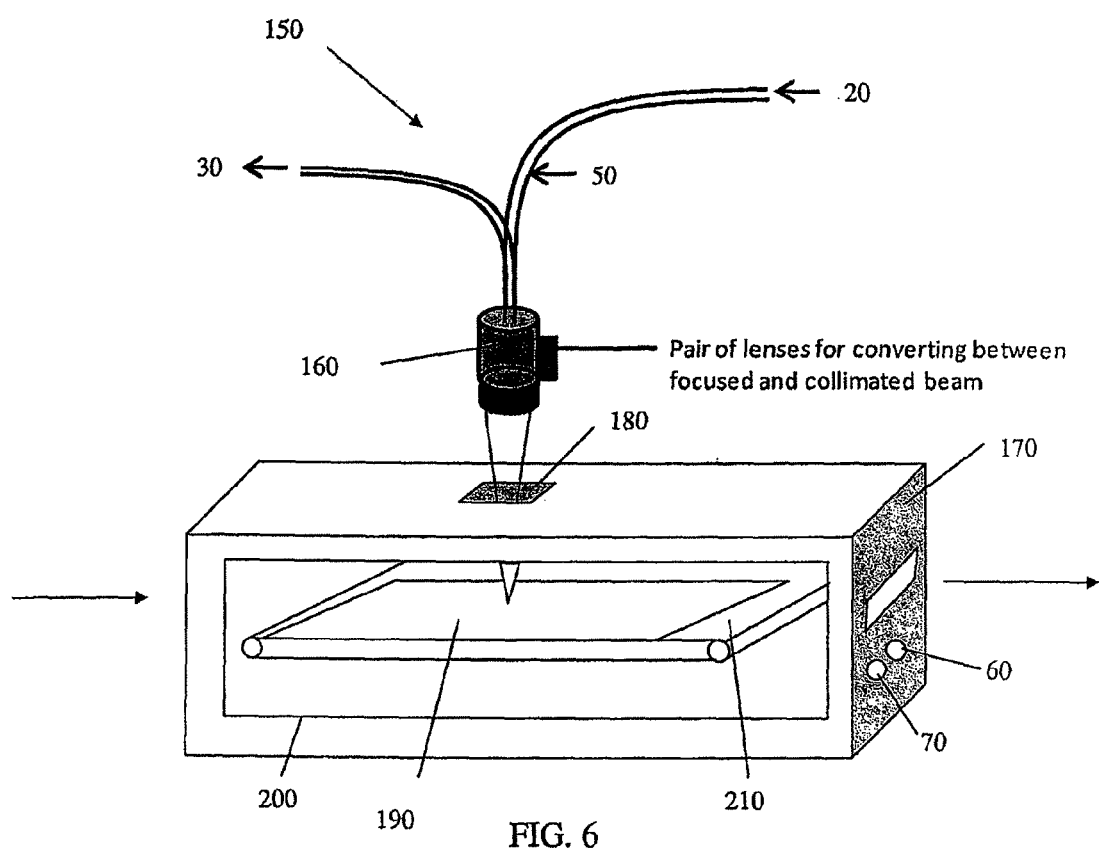
FIG. 6 is an embodiment of in-line system for measuring photoluminescence of a material.

FIG. 6 depicts an embodiment of an in-line temperature corrected photoluminescent measurement system 150. Light from light source 20 is directed, for example, by first optical fiber 50 to apparatus head 160, which can include a lens or any suitable combination of lenses to focus the light into process chamber 170. Apparatus head 160 can be configured to convert focused light from light source 20 to collimated light, back to focused light directed toward the substrate position on substrate 190. Apparatus head 160 can be configured to convert light emitted from the material on substrate 190 to collimated light, back to focused light that is coupled to spectrometer 30.

The light can be directed into process chamber 170, through window 180, which can include a material that is transmissive to the light from light source 20. Window 180 can be optically neutral or can include lens or set of lenses (or other optical components) necessary to transform the light as required. If the necessary lens or multiple lenses or other optical components are included in window 180, apparatus head 160 may be designed without optical components. Light from light source 20 is directed into process chamber 170 toward substrate 190 comprising a material (such as a semiconductor material) deposited on a surface thereof. As viewed through process chamber cutaway 200, substrate 190 can be conveyed to a substrate position within process chamber 170 by conveyor 210. Conveyor 210 can include any suitable components, including a belt and/or one or more rollers sufficient to convey substrate 190 through process chamber 170.

The interior of process chamber 170 can have any suitable ambient environment. For example, interior of process chamber 170 be a high temperature consistent with solar module processing. For example, the interior of process chamber 170 can have a temperature greater than about 25 degrees C., greater than about 50 degrees C., or greater than about 100 degrees C. Process chamber 170 can have a temperature of about 25 degrees C. to about 400 degrees C., about 25 degrees C. to about 300 degrees C., or about 25 degrees to about 200 degrees C. Process chamber 170 can have a temperature of about 25 degrees C. to about 75 degrees C., or about 75 degrees C. to about 100 degrees C., about 100 degrees C. to about 200 degrees C., about 200 degrees C. to about 300 degrees C., or about 300 degrees C. to about 400 degrees C. Process chamber 170 can be about 125 degrees C. to about 175 degrees C. The interior of process chamber 170 can include a gas environment including an oxygen concentration. The oxygen concentration of process chamber 170 can be regulated by adding an inert gas, such as nitrogen, to the interior of process chamber 170 through gas inlet 60.

Temperature measurements in in-line temperature corrected photoluminescent measurement system 150 can be taken for substrate 190 moving continuously through process chamber 170 or in a stop-and-go fashion, wherein substrate 190 pauses at a substrate position in process chamber 170. For measurements for which substrate 190 moves continuously through process chamber 170, the photoluminescent signal is integrated over the area translated under the measurement spot, i.e., the area along substrate 190 that is at some point illuminated by the light from light source 20. For stop-and-go processing, the signal originates from the area on substrate 190 illuminated by the light from light source 20 during the PL measurement. The ability to correct photoluminescent data for temperature allows accurate PL data to be obtained if there is temperature variation within substrate 190 itself.

Process chamber 170 can have ports for any desired measurement devices. For example, process chamber 170 can include a port for a temperature measuring device, such as thermocouple inlet port 70. Thermocouple inlet port 70 can direct a thermocouple connection to the interior of process chamber 170. A thermocouple or other temperature measuring device can take a temperature of the material deposited on substrate 190 at the location where light from light source 20 is directed. Alternatively, temperature measurements from multiple locations can be taken and a material temperature interpolated. Process chamber 170 can include any suitable ports for other measurement devices to measure other characteristics of the ambient contained in process chamber 170, such as oxygen content and/or water vapor content.

Figure 7:
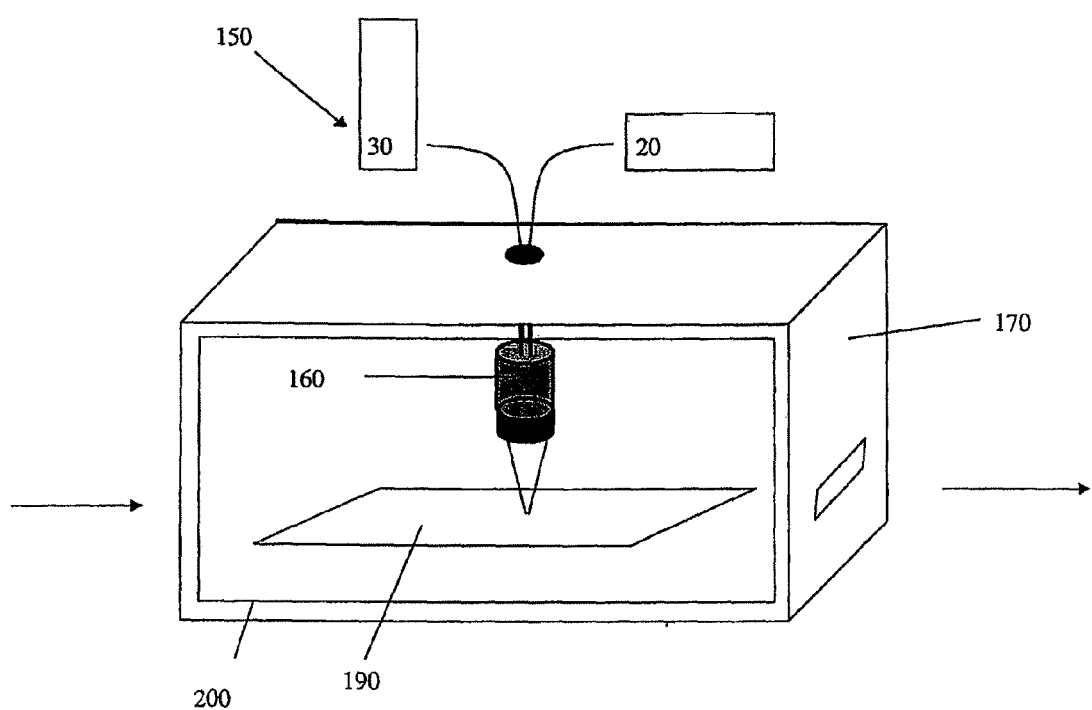
FIG. 7 is an embodiment of in-line system for measuring photoluminescence of a material.

FIG. 7 depicts an alternative embodiment of in-line temperature corrected photoluminescent measurement system 150, where apparatus head 160 is contained in process chamber 170, as visible through process chamber cutaway 200. Light from light source 20 is directed (for example, along a first optical fiber) through a wall of process chamber 170 to apparatus head 160, which can include a lens or multiple lenses, or any other suitable optical components to transform the light (e.g., focus the light) toward substrate 190 so the PL measurements can be taken. The material on substrate 190 being analyzed reemits light back towards apparatus head 160, which transforms the light as necessary and directs the light (for example, along a second optical fiber) towards spectrometer 30.

Details of one or more embodiments are set forth in the accompanying drawings and description. Other features, objects, and advantages will be apparent from the description, drawings, and claims. Although a number of embodiments of the invention have been described, it will be understood that various modifications may be made without departing from the spirit and scope of the invention. In particular, steps depicted in figures may be executed in orders differing from the orders depicted. For example, steps may be performed concurrently or in alternate orders from those depicted. It should also be understood that the appended drawings are not necessarily to scale, presenting a somewhat simplified representation of various features and basic principles of the invention.

What is claimed is:

1. An in-line apparatus for measuring photoluminescence from a material on a substrate in a manufacturing process, comprising:
    a light source configured to direct light along a light path through a lens onto a material deposited on a substrate positioned in a process chamber;
    a spectrometer configured to receive light emitted from the material and generate photoluminescence data for the material; and
    a temperature measurement device configured to measure the temperature of the material.

2. The apparatus of claim 1, wherein the light source comprises a laser.

3. The apparatus of claim 2, wherein the laser has a power ranging from about 0 mW to about 400 mW.

4. The apparatus of claim 3, wherein the laser has a power ranging from about 30 mW to about 100 mW.

5. The apparatus of claim 1, wherein the lens is configured to focus the light onto the material with a spot size of less than about 3 mm$^2$.

6. The apparatus of claim 1, wherein the lens is configured to focus the light onto the material with a spot size of about 1 mm$^2$.

7. The apparatus of claim 1, wherein the temperature measurement device comprises an infrared pyrometer.

8. The apparatus of claim 1, further comprising a first optical fiber to direct light from the light source.

9. The apparatus of claim 8, further comprising a second optical fiber to transmit the light emitted from the material.

10. The apparatus of claim 1, further comprising a computer configured to receive a high-temperature photoluminescence data set from the spectrometer and a measured temperature from the temperature measurement device.

11. The apparatus of claim 10, wherein the computer comprises:
    a low-temperature photoluminescence data set; and a temperature correction equation describing the relation of photoluminescence to temperature for the material.

12. The apparatus of claim 11, wherein the computer reads the measured temperature and applies the temperature correction equation to the high-temperature photoluminescence data set to produce a temperature-corrected photoluminescence data set.

13. The apparatus of claim 12, wherein the computer compares the temperature-corrected photoluminescence data set to the low-temperature photoluminescence data set.

14. The apparatus of claim 12, wherein the computer identifies material properties of the material based upon the temperature-corrected photoluminescence data set.

15. The apparatus of claim 14, wherein the material properties include bandgap.

16. The apparatus of claim 14, wherein the material properties include defect density.

17. The apparatus of claim 16, wherein the module manufacture temperature range is between 25 degrees C. and 300 degrees C.

18. The apparatus of claim 14, wherein the material properties include recombination mechanisms.

19. The apparatus of claim 1, further comprising at least one additional lens through which the light passes and is converted between a focused light beam and a collimated light beam.

20. A system for measuring photoluminescence from a material on a substrate in a manufacturing process, comprising:
    a substrate process chamber;
    a light source configured to direct light along a light path through a first lens toward a substrate position in the process chamber;
    a spectrometer configured to receive light emitted from the material and generate photoluminescence data for the material;
    a temperature measurement device configured to measure the temperature of the material; and
    at least one additional measurement device configured to measure a characteristic of the process chamber environment.

21. The system of claim 20, further comprising a substrate positioned at the substrate position in the process chamber.

22. The system of claim 21, wherein the substrate comprises a material deposited on the surface of the substrate.

23. The system of claim 22, wherein the material comprises a semiconductor material.

24. The system of claim 23, wherein the semiconductor material comprises copper indium gallium (di)selenide.

25. The system of claim 23, wherein the semiconductor material comprises cadmium telluride.

26. The system of claim 20, further comprising a second lens positioned proximate to the first lens to form an apparatus head configured to convert focused light to collimated light.

27. The system of claim 26, wherein the apparatus head is configured to convert collimated light to focused light.

28. The system of claim 26, wherein the apparatus head is positioned in the process chamber.

29. The system of claim 26, wherein the apparatus head is positioned outside the process chamber and the process chamber comprises a window to allow light from the light source to be directed into the process chamber.

30. The system of claim 26, further comprising a first optical fiber to direct light from the light source to the apparatus head.

31. The system of claim 30, further comprising a second optical fiber to transmit light from the apparatus head to the spectrometer.

32. The system of claim 20, wherein the at least one additional measurement device comprises a water vapor measurement device configured to measure the water vapor concentration inside the process chamber.

33. The system of claim 20, wherein the at least one additional measurement device comprises an oxygen measurement device configured to measure the oxygen concentration inside the process chamber.

34. The system of claim 33, further comprising a computer configured to correct photoluminescence data obtained from the material, wherein the correction is based on one or more of material temperature, oxygen concentration inside the process chamber, or water concentration inside the process chamber.

35. The system of claim 20, further comprising a conveyor configured to position the substrate at the substrate position in the process chamber.

36. The system of claim 20, wherein the substrate has a temperature of between about 25 degrees C. and about 400 degrees C.

37. The system of claim 20, wherein the substrate has a temperature of between about 25 degrees C. and about 300 degrees C.

38. The system of claim 20, wherein the substrate has a temperature of between about 25 degrees C. and about 200 degrees C.

* * * * *